(12) United States Patent
Blaser et al.

(10) Patent No.: US 12,114,869 B2
(45) Date of Patent: Oct. 15, 2024

(54) CALCAR GRINDER

(71) Applicant: Smith & Nephew Orthopaedics AG, Zug (CH)

(72) Inventors: Karin Franziska Blaser, Koniz BE (CH); Konrad Schaller, Grenchen SO (CH)

(73) Assignee: Smith & Nephew Orthopaedics AG, Zug (CH)

( * ) Notice: Subject to any disclaimer, the term of this patent is extended or adjusted under 35 U.S.C. 154(b) by 496 days.

(21) Appl. No.: 17/428,333

(22) PCT Filed: Feb. 5, 2020

(86) PCT No.: PCT/EP2020/052885
§ 371 (c)(1),
(2) Date: Aug. 4, 2021

(87) PCT Pub. No.: WO2020/161196
PCT Pub. Date: Aug. 13, 2020

(65) Prior Publication Data
US 2022/0104835 A1  Apr. 7, 2022

(30) Foreign Application Priority Data
Feb. 5, 2019 (GB) .................... 1901589

(51) Int. Cl.
*A61B 17/16* (2006.01)
*A61B 17/56* (2006.01)
*A61F 2/46* (2006.01)

(52) U.S. Cl.
CPC ...... *A61B 17/1659* (2013.01); *A61B 17/1615* (2013.01); *A61B 2017/564* (2013.01); *A61F 2/4607* (2013.01)

(58) Field of Classification Search
CPC ............ A61B 17/1662; A61B 17/1664; A61B 17/1659; A61B 17/1666; A61B 17/1668; A61B 2017/1602
See application file for complete search history.

(56) References Cited

U.S. PATENT DOCUMENTS 5,019,108 A    5/1991  Bertin et al.
6,322,564 B1 * 11/2001 Surma ................... A61F 2/4607
                                                          606/89
8,709,012 B2 *  4/2014 Muller ............... A61B 17/1666
                                                          606/79

(Continued)

FOREIGN PATENT DOCUMENTS

CN    201701256 U    1/2011
WO    WO01/34039 A1  5/2001

OTHER PUBLICATIONS

International Search Report and Written Opinion for International Application No. PCT/EP2020/052885, mailed Jun. 23, 2020.

(Continued)

*Primary Examiner* — Si Ming Ku
(74) *Attorney, Agent, or Firm* — KDW Firm PLLC

(57) ABSTRACT

Apparatus and methods for removing bone and/or tissue at a target location are disclosed. The apparatus comprises a shaft member having a drive end securable to a rotating drive unit, and a cutting head member at a remaining end of the shaft member distal to the drive end.

15 Claims, 12 Drawing Sheets

(56) References Cited

U.S. PATENT DOCUMENTS

| | | |
|---|---|---|
| 2003/0135219 A1 | 7/2003 | Salyer et al. |
| 2003/0212401 A1 | 11/2003 | Nordman |
| 2007/0093844 A1 | 4/2007 | Dye |
| 2008/0306482 A1 | 12/2008 | Muller |

OTHER PUBLICATIONS

European Patent Office, Examination Report, dated Jul. 17, 2023, 10 pages.

* cited by examiner

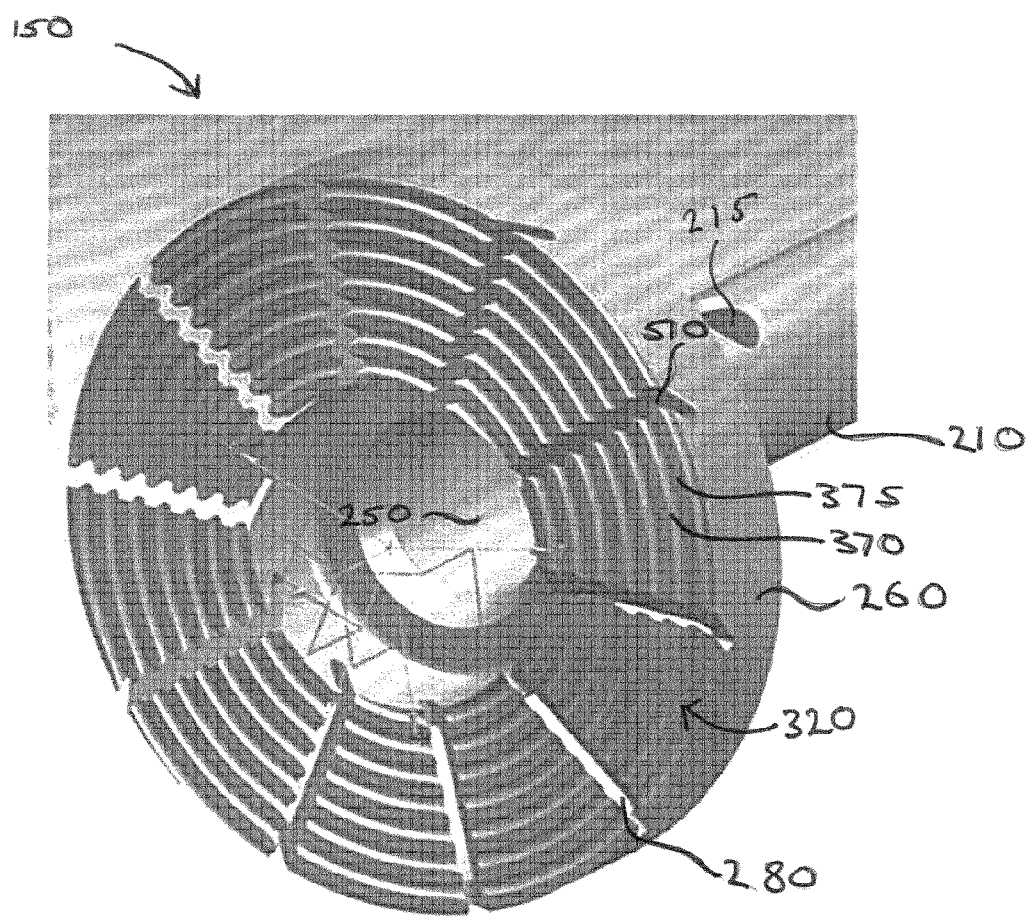
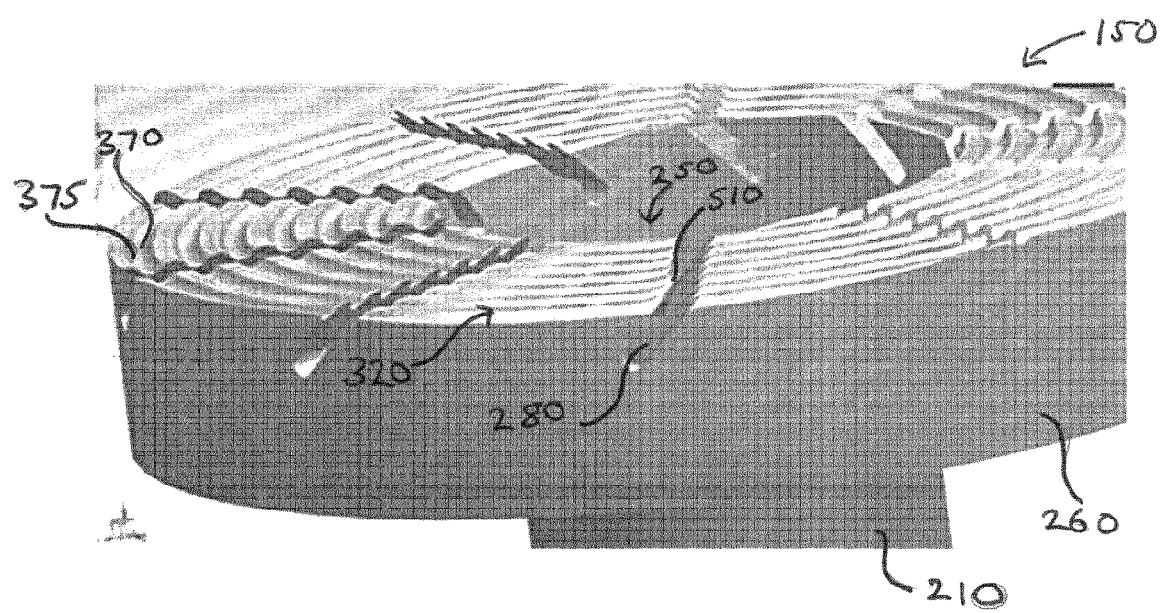
Figure 6

CALCAR GRINDER

CROSS-REFERENCE TO RELATED APPLICATIONS

This application is a United States National Phase filing of International Application No. PCT/EP2020/052885, filed Feb. 5, 2020, which claims priority to, and the benefit of, GB 1901589.8, filed Feb. 5, 2019, the entire contents of each application is hereby incorporated by reference in its entirety.

The present invention relates to medical apparatus and methods for grinding bone and/or soft tissue during surgery. In particular, but not exclusively, the present invention relates to apparatus and methods for removing a portion of the femur, known as the calcar, during preparation of a femoral stem implant in hip joint replacement surgery.

Calcar reamers or grinders are used during surgery to prepare a femoral calcar prior to fitting a prosthetic stem implant and installing a collar or prosthetic femoral head component onto the femoral stem implant to support a synthetic hip joint. Conventional calcar grinders comprise a head end, a shaft member and a connector end. The head end includes a cutting head member, the end surface of which has teeth arranged at angles out of the plane of the surface. These teeth engage with bone when the grinder rotates during use. The grinder spins at high revolutions per minute to remove bone as the head of the calcar grinder is brought into contact with the bone.

Use of conventional grinders results in aggressive removal of bone that may result in reduced control of the fitment of the stem implant. The amount of bone removed on each rotation of a conventional calcar grinder is unpredictable. Furthermore, teeth on conventional calcar grinders can engage too aggressively with the bone, imparting significant torque on the bone that may induce a fracture.

Conventional calcar grinders do not effectively enable removed material to escape the working area, resulting in clogging of grinder teeth with ground up bone and soft tissue, making the grinding of the calcar less efficient and less controllable.

It is an aim of the present invention to at least partly mitigate one or more of the above-mentioned problems.

It is an aim of certain embodiments of the present invention to provide less aggressive bone removal by grinding during surgery than is typical for conventional techniques.

It is an aim of certain embodiments of the present invention to provide a grinding tool for removing bone.

It is an aim of certain embodiments of the present invention to expel removed bone and soft tissue during grinding.

It is an aim of certain embodiments of the present invention to provide a grinding tool that can slot over or otherwise become associated with a guide or post element.

It is an aim of certain embodiments of the present invention to provide circumferentially spaced recesses to form radial recessed regions disposed in a head end region of the body of a grinding tool.

It is an aim of certain embodiments of the present invention to provide radially spaced recesses to form circumferential recessed regions disposed in a head end region of the body of a grinding tool.

It is an aim of certain embodiments of the present invention to enable rotation of a calcar grinder with a drive unit.

It is an aim of certain embodiments of the present invention to transfer rotational motion of a connector end to a head member via a shaft member of the calcar grinder.

It is an aim of certain embodiments of the present invention to provide teeth out of the primary plane of the head end surface of the calcar grinder.

It is an aim of certain embodiments of the present invention to provide a method of preparing the surface of the calcar portion of a femur by grinding during surgery.

It is an aim of certain embodiments of the present invention to provide a method of preparing a uniform surface across a femoral stem implant and the calcar portion of the femur for fitment of a collar or femoral head to the femoral stem implant.

It is an aim of certain embodiments of the present invention to provide a method of keeping a grinding tool proximate to a target location during use in surgery.

According to a first aspect of the present invention there is provided apparatus for removing bone and/or tissue at a target location, comprising:
 a shaft member having a drive end securable to a rotating drive unit; and
 a cutting head member at a remaining end of the shaft member distal to the drive end.

Aptly, the cutting head member comprises a cutting head body that is generally cylindrical and has a generally circular first head member end surface spaced apart from a further head end surface via a cylindrical edge region of the cutting head body.

Aptly, the further head end surface comprises a cutting surface.

Aptly, a central region of the cutting surface is recessed around a position coinciding with a primary longitudinal axis of the shaft member.

Aptly, multiple teeth are disposed along a gently varying or common radius on the cutting surface.

Aptly, multiple teeth are disposed at or close to a predetermined radius from a central axis on the cutting surface.

Aptly, the teeth comprise a plurality of concentric teeth or teeth arranged generally concentrically.

Aptly, multiple teeth are arranged on multiple common concentric circles or on a spiral such as an Archimedean spiral or Fermat's spiral or the like.

Aptly, teeth protrude from a generally circular cutting surface at a distal end of a shaft member.

Aptly, a head member is disposed at an end of a shaft member.

Aptly, a central recess is provided in a circular cutting surface.

Aptly, primary teeth of the cutting head member are spaced circumferentially around a cutting surface.

Aptly, each primary tooth carries a plurality of secondary teeth.

Aptly, each primary tooth is spaced apart from each adjacent primary tooth via a radially extending channel.

Aptly, each channel comprises a radially extending elongate recess in a circular cutting surface.

Aptly, the first head member end surface comprises an annular recess centred around a primary longitudinal axis of the shaft member.

Aptly, the radially extending elongate recess comprises a curved bottom surface.

Aptly, the radially extending elongate recess provided in the further head end surface intersects the annular recess provided in the first head member end surface.

Aptly, the radially extending elongate recess has a droplet profile.

Aptly, the cutting head member comprises at least one through slot for delivering fluid to the target location.

Aptly, the cutting head member comprises a removable cover configured to cover the annular recess in the first head member end surface.

Aptly, the removable cover comprises a central through hole configured to be slidable over the shaft element.

Aptly, each channel meets a cutting surface at an oblique angle.

Aptly, the oblique angle is about around 30 to 50 degrees with respect to a longitudinal axis associated with the shaft.

Aptly, each secondary tooth comprises an upstanding leading edge that extends away from a plane associated with the cutting head.

Aptly each secondary tooth further comprises a trailing edge region that lies in a primary plane associated with a cutting surface.

According to a further aspect of the present invention there is provided a method of removing bone and/or tissue at a target location, comprising the steps of:
  locating a cutting head having a central recess in a cutting surface of the cutting head proximate to a bone and locating a post element associated with the bone within the recess to position the cutting head at a target location;
  via a drive unit, rotating a shaft member that is arranged to move with the cutting head; and
  cutting bone at the target location via a cutting surface of the cutting head that comprises primary and secondary cutting teeth.

Aptly, the method further comprises removing bone from the cutting surface of the cutting head member as the shaft member rotates.

Aptly, the method further comprises removing bone from the cutting surface of the cutting head via at least one radially extending channel in the cutting head.

Aptly, the method further comprises removing bone from the cutting surface of the cutting head via at least one circumferentially extending channel in the cutting head.

Aptly, the method further comprises removing bone from the cutting surface of the cutting head via a spirally extending channel in the cutting head.

Aptly, the method further comprises delivering fluids to the target location via at least one through hole in the cutting head.

Aptly, the method further comprises removing bone from the cutting surface of the cutting head via at least one through hole in the cutting head.

Aptly, the method further comprises cutting bone and/or tissue at the target location via a conventional 'rough' calcar grinder prior to the previous steps to achieve a 'rough' then more precise cutting process.

Certain embodiments of the present invention enable expulsion of removed material via channels in the form of elongate recessed regions in the cutting surface of the cutting head member.

Certain embodiments of the present invention enable expulsion of removed material via one or more channels each arranged as a single continuous recessed region spiralling outward from the centre to outer edge of the surface of the cutting head member.

Certain embodiments of the present invention provide less aggressive removal of bone and/or tissue during surgery than conventional techniques permit using teeth spaced apart by recessed regions.

Certain embodiments of the present invention provide a uniform surface across a femoral stem implant and the calcar portion of the femur by keeping the grinding tool proximate to a target location during surgery.

Certain embodiments of the present invention provide an efficient method of grinding bone and/or tissue by removing debris in the form of bone and/or soft tissue from the target location during grinding.

Embodiments of the present invention will now be described hereinafter, by way of example only, with reference to the accompanying drawings in which:

FIG. 6 illustrates further views of a grinder/cutting tool;

In the drawings like reference numerals refer to like parts.

Figure 1:
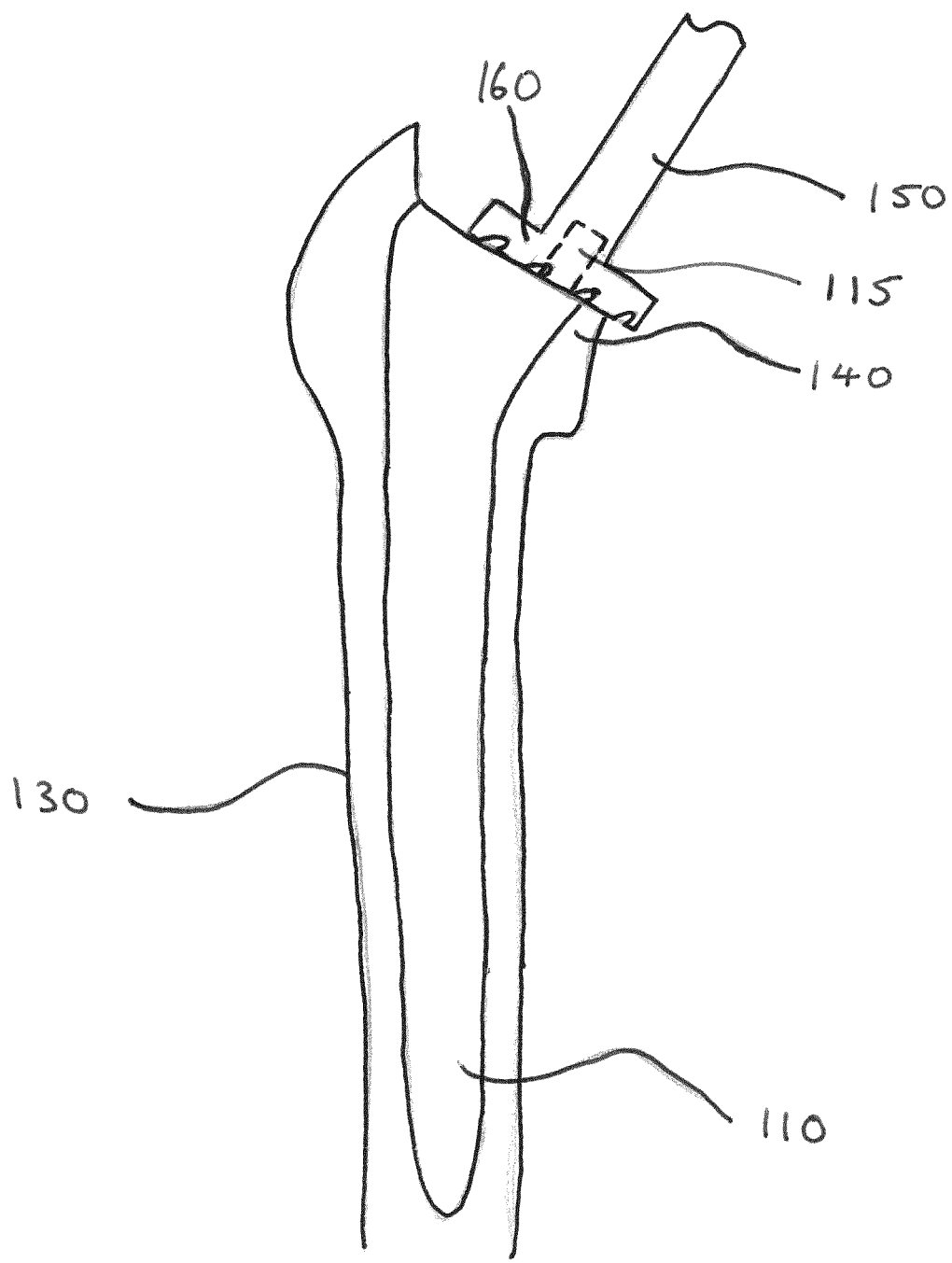
FIG. 1 illustrates preparation of a femur prior to fitment of a prosthetic component in the form of a stem implant using a calcar grinder.

FIG. 1 illustrates preparation of a target location provided by a trial stem 110 in a natural femur 130 in order to fit a femoral neck collar (not shown) to a prosthetic stem implant (not shown). A uniform surface across the top of a prosthetic stem implant and a portion of the calcar 140 of the femur 130 is required to provide correct fitment of a femoral neck collar. The uniform surface is prepared by grinding the calcar 140 with a calcar grinder 150, which has a connector end (not shown) and a head end 160 distal from the connector end. The head end 160 includes teeth for engaging with the calcar 140. The trial stem 110 may include a guide or post element 115 over which the calcar grinder 150 may mount by slotting a recessed portion of the calcar grinder 150 over the post element. The post element may optionally act as a stop limit for the calcar grinder. A stop limit helps to prevent a surgeon from over grinding the femur.

During surgery, the calcar grinder may be rotated by a drive unit (not shown in FIG. 1) coupled to the calcar grinder 150 via the connector end (not shown in FIG. 1). The calcar grinder may be positioned over the post element 115 to keep the calcar grinder proximate to a target location, the target location being proximate to the calcar portion 140 of the femur 130. In combination with the trial stem 110, this helps keep the grinder 150 at a predetermined angle relative to the femur 130 in order to help reproducibly prepare the femur for 130 fitting a femoral neck collar and prosthetic stem implant (not shown). Once in position, rotation of the head end 160 of the calcar grinder 150 whilst in contact with the target location removes bone from the target location.

Figure 2:
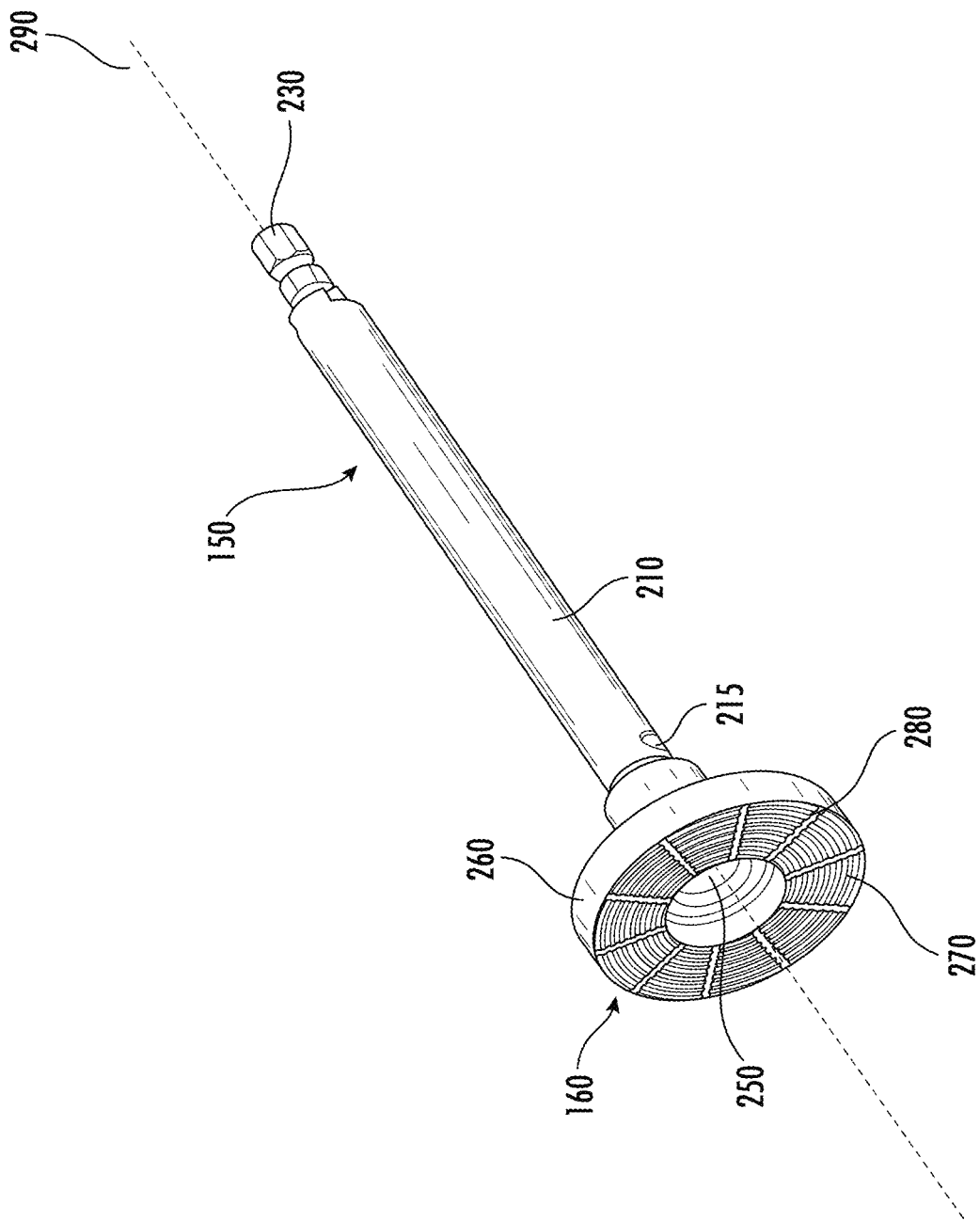
FIG. 2 illustrates an embodiment of a calcar grinder.

FIG. 2 shows an embodiment of the calcar grinder 150. The calcar grinder 150 has a shaft member 210 between a connector end 230 and a head end 160. The head end 160 comprises a cutting head member 260 and is distal from the connector end 230. The connector end 230 is shaped to engage with an appropriate drive unit (not shown) in order to spin the calcar grinder 150 during use. The connector end 230 may have a prismatic shape. Optionally, the connector end 210 may have a cylindrical shape. The calcar grinder 150 has a longitudinal axis 290 associated with the shaft.

In the example embodiment the shaft 210 is an elongate cylindrical portion of the body of calcar grinder 150. Optionally, the shaft member 210 may be an elongate prismatic portion of the body of the calcar grinder 150. The shaft member 210 is disposed to transfer rotational motion between the connector end 230 and the cutting head member 260. The shaft member 210 may have first and further portions wherein the diameter of the shaft member 210 varies between the first and further portions.

The cutting head member 260 may have a cutting head body that is generally cylindrical and has a generally circular first head member end surface spaced apart from a further head end surface via a cylindrical edge region of the cutting head body. The cutting head member 260 may have a primary recessed region 250 centred around the longitudinal axis 290 of the body of the calcar grinder 150. The primary recessed region 250 extends into cutting head body of cutting head member 260 along the longitudinal axis 290 of the body of the calcar grinder 150. The primary recessed region 250 may be shaped to fit over a post element 115 of a trial stem 110. Optionally, the recessed region 250 may have multiple diameters along its depth. Aptly, the recessed region 250 may be stepped in order to provide an abutting surface for the calcar grinder that may provide a stop limit. Optionally, the recessed region 250 may be shaped to receive a bearing or bushing positioned about the post element 115. This may reduce friction and/or vibration between the trial stem 110 and the calcar grinder 150. Aptly, the diameter of the recessed region 250 may be determined by the width of the trial stem 110. Configuring the diameter of the recessed region 250 to the width of the trial stem 110 may help to prevent the grinder from cutting the trial stem which may introduce unwanted materials to the cutting site. For example, cutting a metal or plastic trial stem may otherwise damage the cutting surface of the calcar grinder and/or contaminate the cutting site.

A through slot 215 is shown disposed in the side of the shaft member 210 towards the distal end of the shaft. The through hole may be provided between an outer surface of the shaft 210 and the recessed region 250. The through hole 215 in the shaft 210 may be provided to help clean debris from the recessed region 250 during or after surgery. For example, fluid may be flushed through the hole 215 in the shaft 210 into the recess 250 to help remove debris from the recess.

The cutting head body of the cutting head member 260 may have at least one elongate radially extending recessed region 280 disposed circumferentially about and coinciding with the longitudinal axis 290 of the body of the calcar grinder 150. Each radial recessed region 280 may extend from the first head member end surface into the cutting head body of the cutting head member 260 at an oblique angle to the longitudinal axis 290. The cutting head body of the cutting head member 260 may have at least one circumferential recessed region 270 disposed radially from the longitudinal axis and extending circumferentially around the longitudinal axis 290 of the calcar grinder 150. Provision of radial 280 and circumferential 270 recessed regions helps the cutting head member clear bone and/or tissue removed from the femur 130, thus helping to prevent the surface of the cutting head member 260 from clogging up with bone and/or tissue removed by the grinder. As the calcar grinder 150 is rotated around its longitudinal axis 290, material removed from the femur 130 by the cutting head member 260 is forced away from the cutting surface through the radial recessed regions 280.

Figure 3:
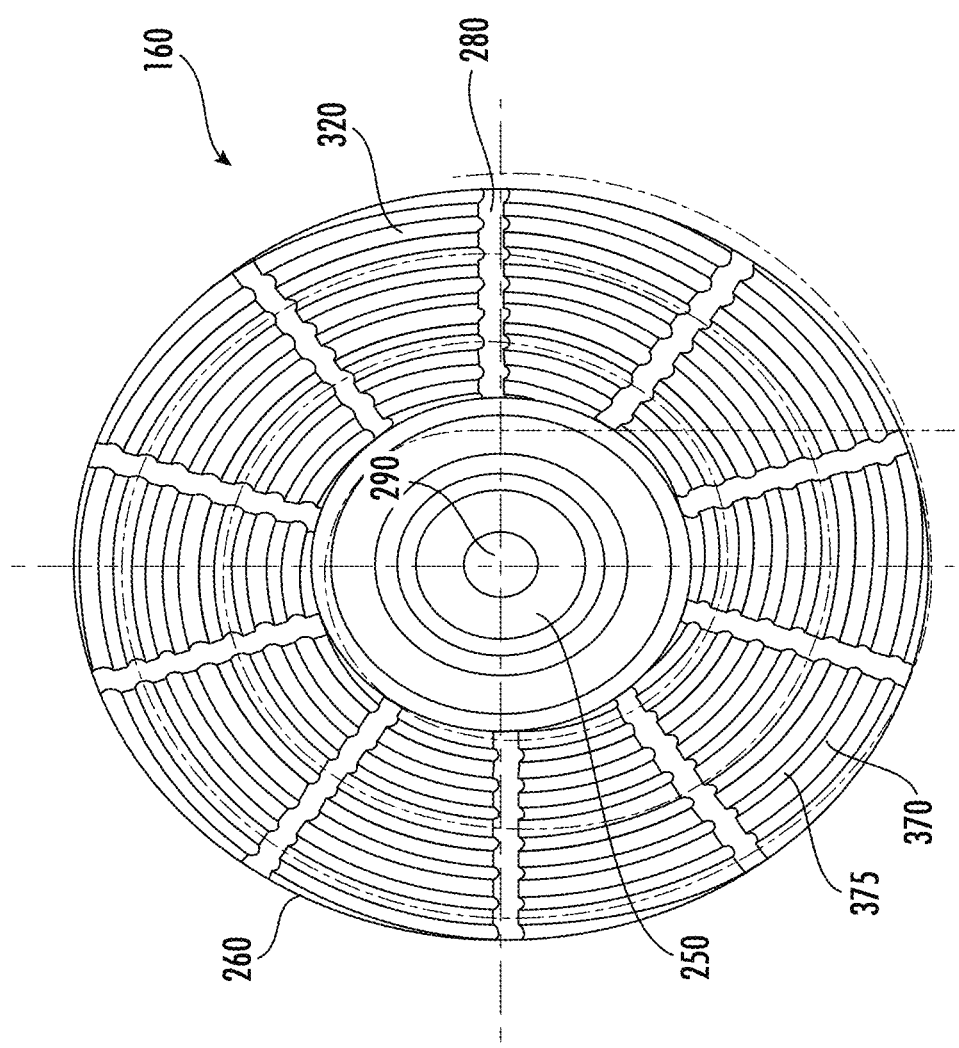
FIG. 3 illustrates an end on view of the cutting surface at a head end of the calcar grinder.

FIG. 3 illustrates an end on view of the head end 160 and thus a cutting surface of the calcar grinder 150. The longitudinal axis 290 extends into and out of the plane of the drawing. The radially extending recessed regions 280 (ten shown in FIG. 3) are shown with wave-like edges to illustrate that the radial recessed regions extend into the cutting head body of the cutting head member 260 at an oblique angle. Disposing a plurality of radial recessed regions in the first head end member surface may separate the first head end member surface into cutting head member islands 320 which may thus be thought of as primary teeth.

In the example embodiment, at least one circumferential recessed region 370 is provided as a single continuous radial recessed region extending radially outwards in a spiral starting from the centre of the first head member end surface to the outer edge of the first head member end surface. Aptly the spiral is an Archimedean-like or Fermat's spiral like curve. Optionally, multiple spirally extending recessed regions may be provided in the first head member end surface. Optionally, as an alternative the at least one circumferential recessed region 370 may be a plurality of circumferentially extending radial recessed regions each disposed distinct distances from the centre of the first head member end surface. This provides concentric circles with teeth on them as crests between each of the plurality of circumferentially extending recessed region. Provision of one or more continuous recessed regions arranged in one or more spirals in the first end surface of the cutting head member 260 helps remove material removed by the grinder at the cutting site from the cutting head member, thus helping to prevent the cutting head member from clogging up with material. In certain embodiments, the centre of the first head member end surface may coincide with the longitudinal axis 290. The at least one circumferential recessed region 370 may have a tubular profile. Optionally, the at least one circumferential recessed region 370 may have a polyhedral profile.

The first head member end surface may form a plurality of crests 375 between multiple circumferentially radial recessed regions and/or the radially inner and radially outer edges of the first head end member surface. The crests 375 and recessed region 370 in the first head member end surface provide grinding surfaces and pathways respectively for removal of material cut by the cutting head. Optionally, the width of a crest 375 is tapered towards a point where the at least one circumferential recessed region 370 meets the edge of a cutting head member island 320. Rotating the cutting head 260 via the drive unit and shaft 210 at a surgical site results in cutting of bone and/or tissue as teeth on the cutting surface of the head engage with the bone. Removed bone is then driven away from the cutting surface through the circumferential and/or radial recessed regions 370, 280 as the cutting head rotates.

Figure 4:
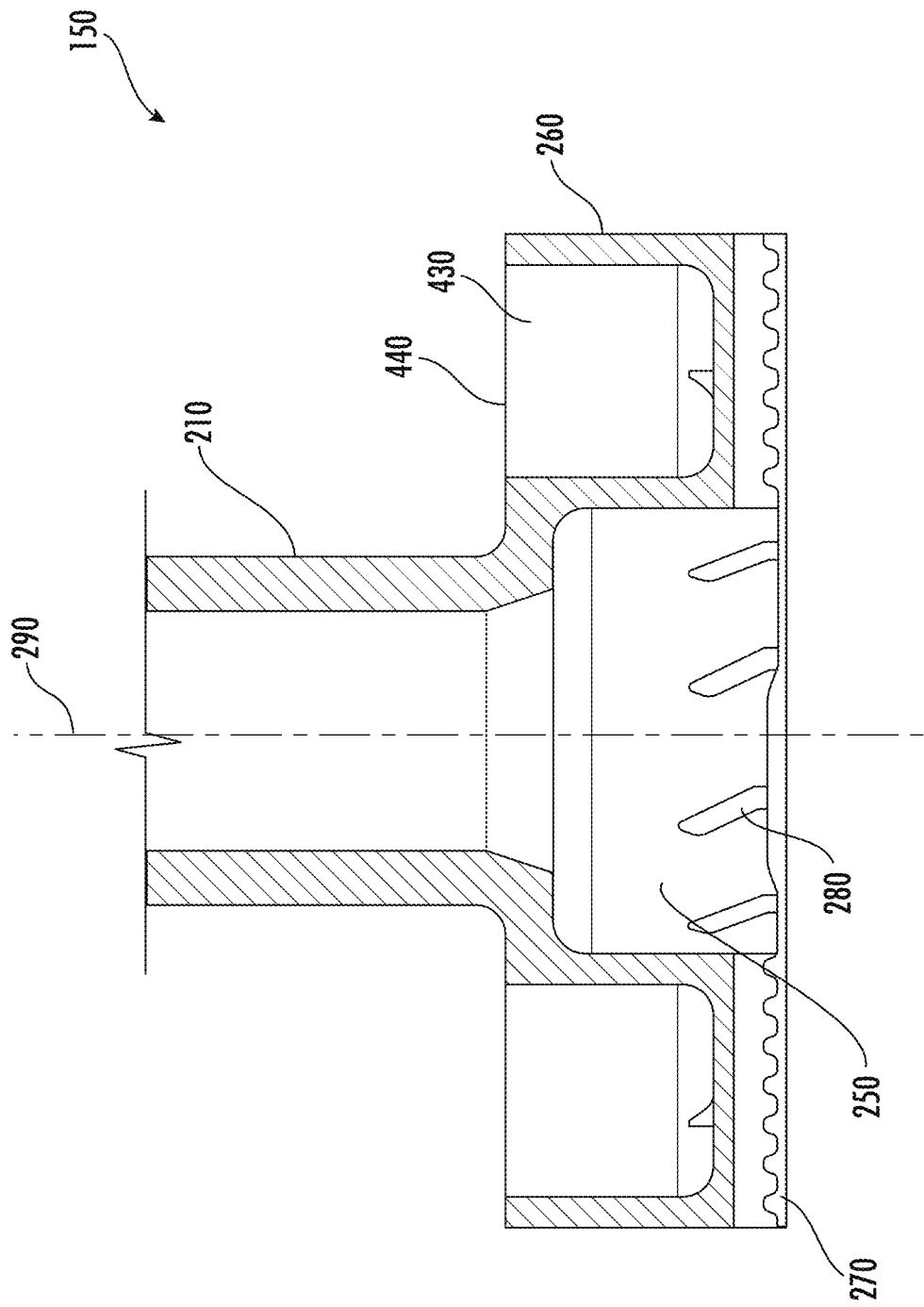
FIG. 4 illustrates a cross-sectional side view of the head end of the calcar grinder.

FIG. 4 illustrates an example embodiment of the cutting head member 260. A cross section view of a portion of the calcar grinder 150 is illustrated, showing how the cutting head body of the cutting head member 260 and the shaft member 210 blend to form the calcar grinder 150. Alternatively, the shaft 210 and the cutting head member 260 of the calcar grinder 150 may be formed of two separate pieces secured together. The primary recessed region 250 is shown extending from the first head member end surface/cutting surface into the cutting head body of the cutting head member 260 and intersecting the at least one radial recessed region 280. Optionally, the primary recessed region 250 may also extend into the shaft member 210. Optionally, the recessed region 250 may have multiple diameters along its depth. Aptly, the recessed region 250 may be stepped in order to provide a stop limit for the calcar grinder. Optionally, the recessed region 250 may be shaped to receive a bearing or bushing positioned about the post element 115. This may help to reduce friction and/or vibration between the trial stem 110 and the calcar grinder 150. Aptly, the diameter of the recessed region 250 may be determined by the width of the trial stem 110. Configuring the diameter of the recessed region 250 to the width of the trial stem 110 may help to prevent the grinder from cutting the trial stem which may introduce debris to the cutting site. For example, cutting a metal or plastic trial stem may damage the cutting surface of the calcar grinder and/or contaminate the cutting site. Aptly, the recessed region 250 may coincide with a through hole in the shaft 210, providing a pathway for fluid through the recessed region to help with cleaning the calcar grinder during or after surgery.

In the example embodiment shown in FIG. 4, a relieving recessed region 430 may extend from the further head end member surface 440 into the cutting head body of the cutting head member 260. The relieving radial recessed regions may extend sufficiently into the cutting head member 260 that the relieving radial recessed regions 430 may intersect the at least one radial recessed region 280, such that the at least one radial recessed region forms at least one through hole or slot between the first head end member surface and the further head end member surface through the cutting head member 260. Alternatively, the head may be a generally solid body with a smooth circular rear surface.

Providing a through hole from the first head end member surface into the relieving radial recessed regions 430 has the advantage of allowing removed material such as bone and soft tissue to clear the area of the calcar being ground by the calcar grinder. The through hole may also enable a user to administer fluids to the cutting area. For example, cutting lubricants, wound cleaning fluids and anaesthetic fluids may be delivered to a cutting site during surgery. Aptly, a saline solution (NaCl) may be delivered to a cutting site to help clean the site or wound. Aptly, the saline solution (NaCl) may be delivered to a cutting site to help reduce heating due to friction at a cutting site. The relieving radial recessed regions 430 extends in a circle about the longitudinal axis 290. Optionally, a cover (not shown) may be provided that is configured to fit around the relieving radial recessed regions 430. Optionally, the cover may be secured around the relieving radial recessed regions 430 via an interference fit with the cutting head 260 and/or the relieving recessed regions 430. Optionally, the cover may include a port for delivering fluid to a surgical site via through holes in the relieving radial recessed region of the grinder during surgery. A cover may help to protect a user from and/or contain fluids, bone and/or tissue removed from the cutting head through the relieving recessed regions 430.

Figure 5A:
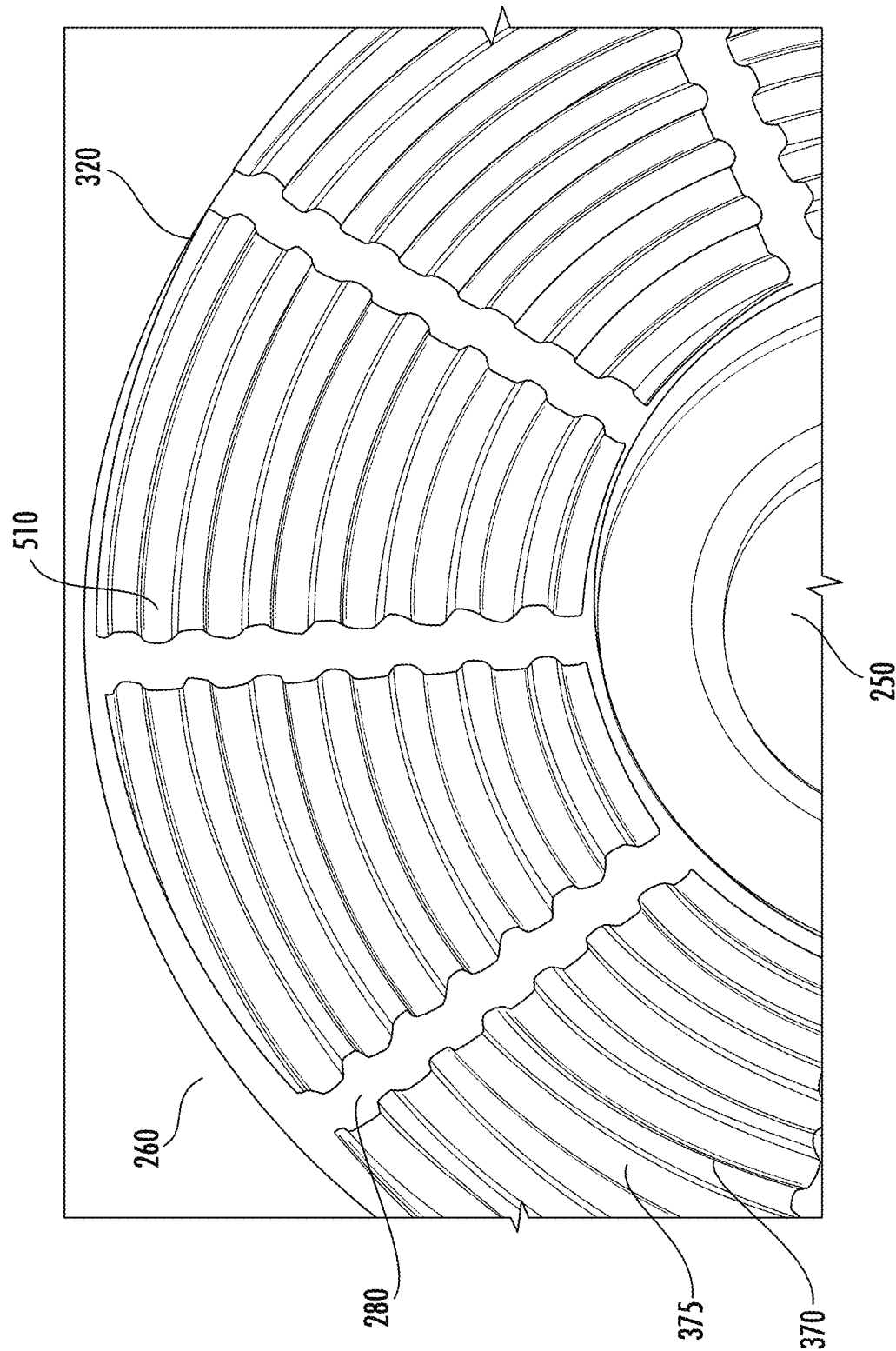
FIG. 5a illustrates a magnified view of a portion of the head end cutting surface of the calcar grinder.

FIG. 5a illustrates a magnified end on view of the cutting head member 260. Thus, part of the cutting surface is shown. The cutting head member 260 shown in FIG. 5a has a solid body, such that the radially recessed regions 280 in the cutting surface extend partially through the connector head body. Optionally, the cutting head 260 may include one or more relieving recessed regions 430, centred about a shaft that intersects the radially recessed regions 280, to provide one or more through holes in the connector head 260. In the example embodiment, the primary recessed region 250 extends into the plane of the drawing, as do radial recessed regions 280, at an oblique angle to the longitudinal axis 290 in order to provide pathways for removal of material from the cutting site to help prevent the calcar grinder form clogging up. The radial recessed regions 280 divide the first head end member surface into cutting head member islands 320 or primary teeth. Each primary tooth includes multiple secondary teeth provided by points at one edge of the cutting head member islands.

The magnified view shows an example embodiment wherein the at least one circumferential recessed region 370 extends as a single continuous spiral starting from the centre of the first head end member surface (not shown). At least one crest 375 may be disposed on the first head end member surface between adjacent revolutions of the at least one circumferential recessed region 370 of the example embodiment. The width of the at least one crest 375 may be greater, equal to, or less than the width of the at least one circumferential recessed region 370. Optionally, the radial width of the crest may vary along the length of the cutting head member island 320.

In the example embodiment, an end portion 510 of the at least one crest 375 may curve out of the plane of the crest surface. This embodiment enables secondary teeth to be provided by each end portion 510, wherein the edge of the cutting head member island meets a radial recessed region 280. Optionally, the end portion 510 may not curve out of the plane of the crest surface, but rather remain in or be recessed in the plane of the crest surface. Modification to the angle of the end portions 510 of the crests 375 relative to the cutting head surface may allow each calcar grinder to have a predefined coarseness, such that a surgeon may choose a calcar grinder during surgery based on how aggressively it cuts the bone. Angling the end portions 510 of the crests 375 into the cutting head surface may also help guide material removed by the grinder into the radially recessed regions 280 in order to remove material from the calcar grinder and prevent the grinder form clogging up. Optionally, the crest width in the end portion 510 may be tapered or straight. For a plurality of crests 375, the crest width of the end portions 510 may be tapered and or straight. Optionally, for a plurality of crests 375, the crest width of the end portions 510 may be in the plane of the crest surface and/or curve out of the plane of the crest surface. Optionally, the crest surface in the end portion 510 kinks, rather than curves out of the plane of the crest surface. Rather than a constant spiral, concentric circles may be used centred on the central longitudinal axis position.

Figure 5B:
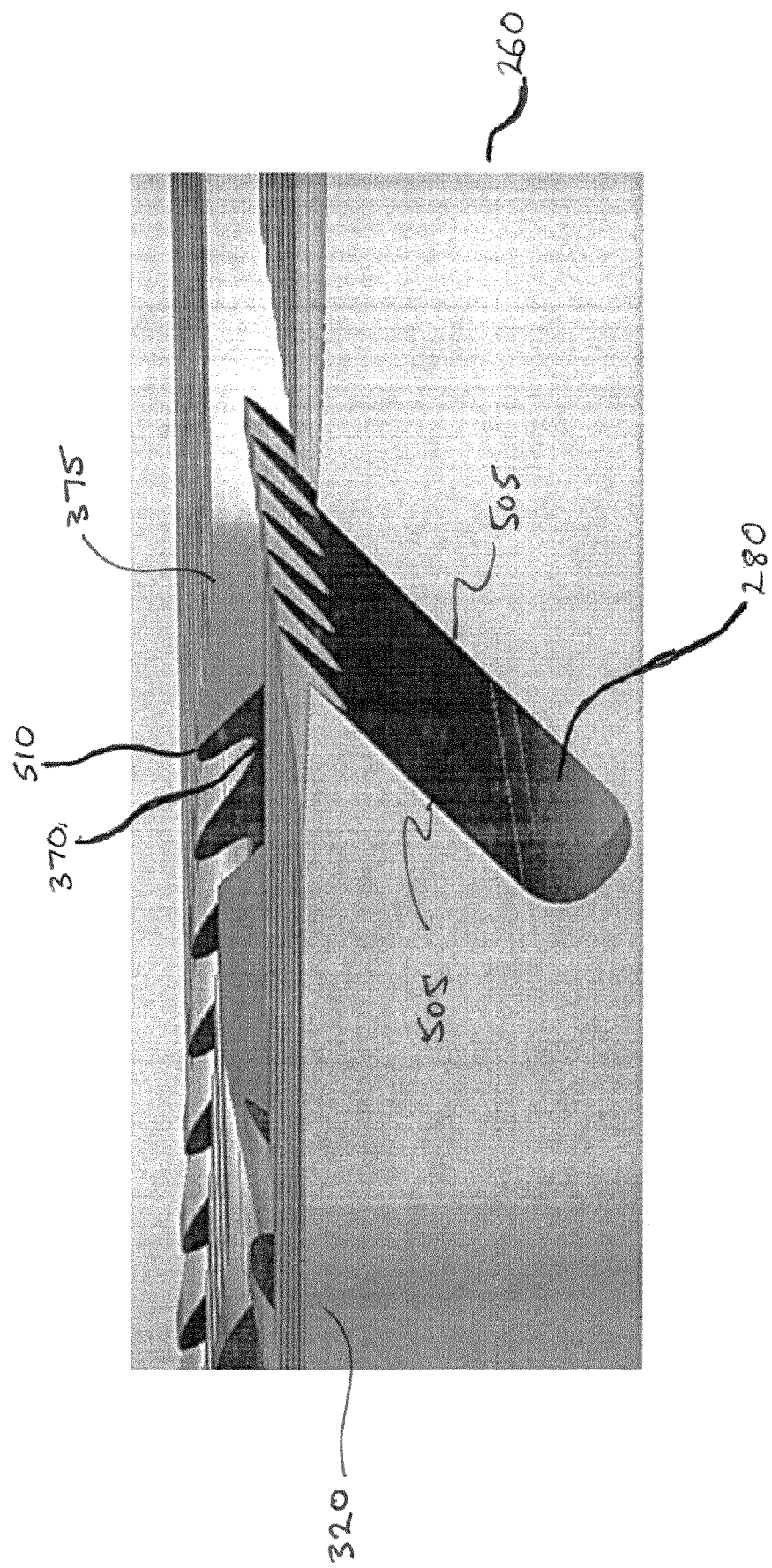
FIG. 5b illustrates a magnified side on view of the head end of the calcar grinder.

FIG. 5b illustrates a magnified side on and end on perspective view of the cutting head member 260. This view of the cutting head member 260 shows the at least one radially extending recessed region 280 separating the first head end member surface into primary teeth or cutting head member islands 320. The oblique angle of the radial recessed regions 280 relative to the longitudinal axis 290 may be about around or between 30 to 50 degrees. Optionally, the surface of cutting head member islands 320 may be tilted out of the plane of the first head end member surface.

The radially extending recessed region 280 is shown with a curved bottom surface. The curved bottom surface may help to prevent material removed by the grinder from binding and clogging up the radially extending recessed region. The radial recessed region 280 is also shown extending through a radial outer surface of the cutting head member 260, thus providing a pathway for removal of material cut away by the grinder during use. Aptly, opposed sidewalls 505 of adjacent primary teeth 320 are spaced apart in a substantially parallel configuration.

The side on view in FIG. 5b shows how an end portion 510 of a crest 375 curves out of the plane of the crest surface to form a secondary tooth at the end of the crest 375 wherein a cutting head member island 320 meets a radial recessed region 280. Optionally, the end portion 510 may remain in the plane of the crest surface 375. Altering the amount that the end portion 510 of the crest 375 curves out of the plane of the cutting head surface may allow a set of calcar grinders of varying coarseness to be designed. Optionally, an end portion 510 may be tapered.

During use the calcar grinder spins to engage the secondary teeth 510 with a femur for preparation of the femur prior to fitting a prosthetic implant. The secondary teeth 510 remove bone as the cutting head rotates. The primary teeth then help guide debris removed by the secondary teeth away from the cutting surface through the circumferential recessed regions 370 and radial recessed regions 280. Crests 375 of the primary teeth may further cut the bone as the cutting head rotates. Aptly, the crests 375 of the primary teeth may smooth the bone surface after the secondary teeth have cut into the bone, thus helping the calcar grinder provide a substantially smooth surface on the calcar of the femur for fitment of a femoral neck collar. Aptly, the circumferential recessed regions of the cutting surface may help fluid administered to the surgical site to be distributed evenly by the cutting head at the surgical site.

FIG. 6 shows further perspective views of the calcar grinder 150. In the top half of FIG. 6, the recessed region 250 of the calcar grinder 150 is illustrated extending through the cutting head member 260 into the shaft 210. In the example calcar grinder shown, the profile of the recessed region 250 is cylindrical. The recess 250 may be configured to engage with a cylindrical post element associated with a trial stem. The calcar grinder shown has a cutting head member end surface divided up in to cutting head member islands 320 by radially extending recessed regions 280. The radial recessed regions 280 are provided at an oblique angle to the surface normal of the cutting head end surface. The radial recessed regions 280 help remove material cut by the grinder from the cutting surface to help prevent the calcar grinder from clogging up with material during use. In the example calcar grinder shown in FIG. 6, a continuous spiral extending recessed region 370 is provided in the cutting head surface. The spiral recessed region 370 provides channels or pathways that help material cut from the surgical site, such as bone and/or tissue, to escape from the cutting surface of cutting head member 260. As the grinder is spinning during use, material cut from a femur by the grinder is forced away from the cutting site though channels such as the spiral recessed regions 370 and radial recessed regions 370. The channels help to prevent debris from clogging the cutting surface of the grinder and damaging the femur.

Between portions of the spirally extending recessed region 370 are crests 375 that form portions of the cutting surface of the cutting head member 260. The crests 375 provide a cutting surface on each cutting head member island 320, thereby providing multiple teeth on each cutting head member island 320 or primary tooth of the cutting head member 260. FIG. 6 shows multiple primary teeth or cutting head member islands 320 circumferentially spaced apart on the surface of the cutting head member 260.

Where a cutting head island 320 meets a radial recessed region 280, a portion 510 of a crest 375 of the cutting head island curves out of the plane of the cutting surface of the cutting head member 260 to form a secondary tooth. In FIG. 6, secondary teeth are provided on one side of each cutting head member island 320. In the example calcar grinder shown, secondary teeth are provided on a counter-clockwise side of each cutting head member island or primary tooth 320. This is shown more clearly in the perspective view of the calcar grinder in the bottom half of FIG. 6.

During use, secondary teeth of the calcar grinder engage with bone and remove parts of the bone to help prepare a femur for fitment of a trial stem and/or femoral neck collar. Bone and/or tissue removed by the secondary teeth may then escape the cutting surface of the cutting head member 260 through circumferential 270 or spiral recessed regions 370 and radial recessed regions 280 in the cutting surface thus helping remove bone material from the calcar grinder by rotational forces on the material as the grinder spins.

Figure 7:
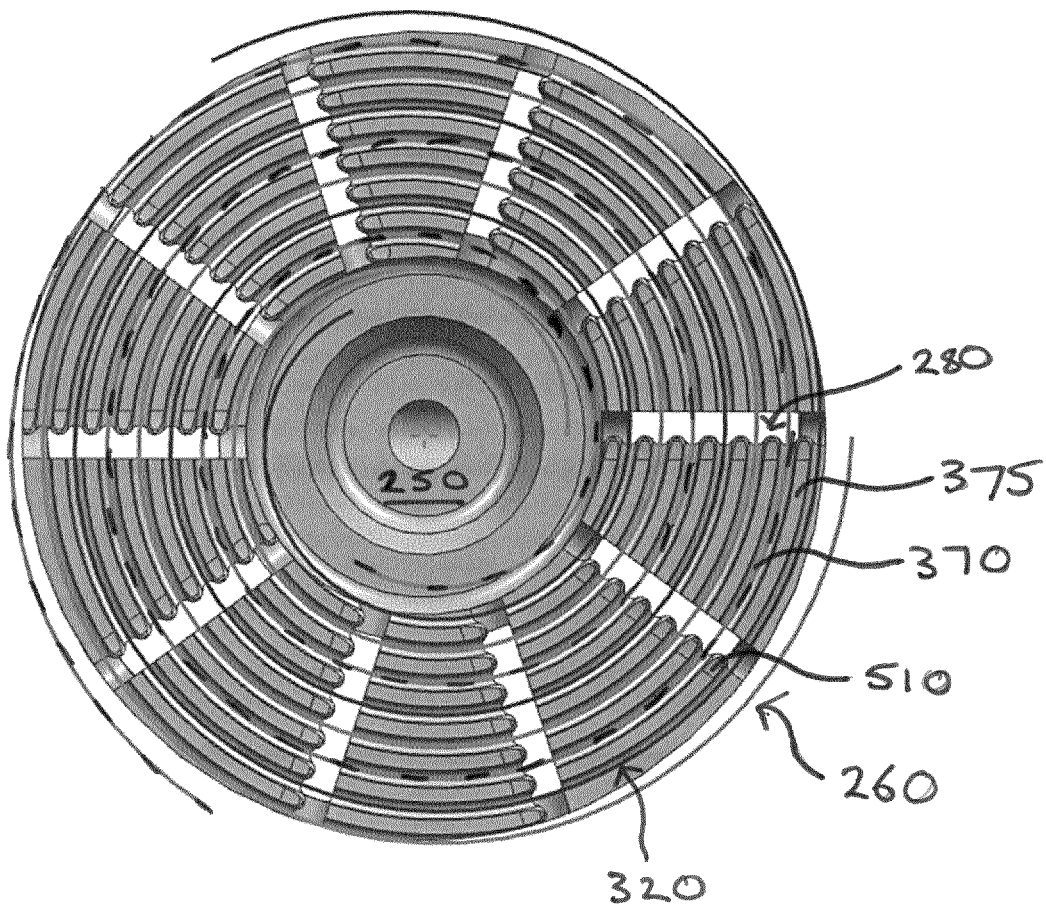
FIG. 7 illustrates an end on view of the head end cutting surface of the calcar grinder.

FIG. 7 illustrates a cutting surface of the calcar grinder viewed along the longitudinal axis 290 of the grinder. Three spirally extending recessed regions 370 are shown in the cutting surface of the cutting head member 260 in FIG. 7, one of which is illustrated by dashed lines. Optionally, a single spirally extending recessed region may be provided in the cutting surface. Optionally, more than one spirally extending recessed region may be provided in the cutting surface. Crests 375 on the surface of the cutting head member 260 are provided between portions of the spirally extending recessed regions. Portions of the three spirally extending recessed regions 370 are separated by radially extending recessed regions 280. The radial recessed regions 280 are shown extending through the cutting head member 260 to provide a through holes in the cutting head member. Providing one or more through holes in the cutting member helps to remove debris from the cutting site during use. Optionally, the radial recessed regions 280 may partially extend into the cutting surface of the cutting head member 260. Radial recessed regions 280 divide the cutting surface up in to cutting head member islands or primary teeth 320. Portions of the crests 375 may extend out of the plane of the cutting surface to provide secondary teeth 510. Secondary teeth 510 may be provided at the edge of a primary tooth 320.

Figure 8:
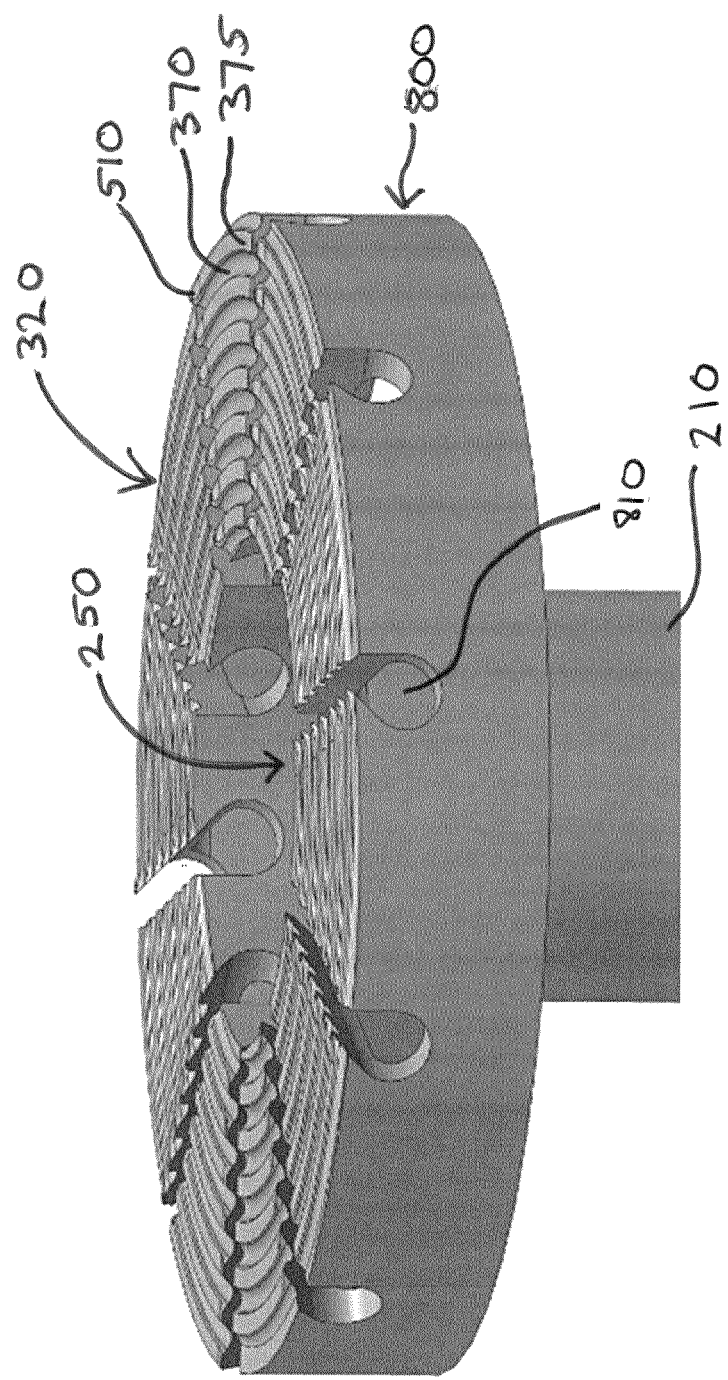
FIG. 8 illustrates an alternative head end of the calcar grinder.

FIG. 8 illustrates an alternative cutting head member 800 of a calcar grinder. The cutting head member 800 is shown in connection with a shaft 210 of the calcar grinder and includes a recessed region 250 in the cutting surface of the cutting head member 800. The cutting surface of the cutting head member 800 includes either spirally extending recessed regions or concentric recessed regions 370 separated by crests 375 on the cutting surface. Portions of the spiral or concentric recessed regions 370 are shown separated by radially extending recessed regions 810, dividing the cutting surface in to cutting head member islands or primary teeth 320. The radial recessed regions shown in FIG. 8 have a droplet profile. The droplet profile or shape helps removal of debris from the cutting site, such that bone chips of various sizes may be removed from the cutting surface without clogging the recessed regions. Aptly, the radial recessed regions 810 extend through the cutting head member 800 to provide one or more through holes. The through holes help remove debris from the cutting site during use. Aptly, the radial recessed regions 810 may extend partially into the cutting surface of the cutting head member 800. Portions of the crests 375 may extend out of the plane of the cutting surface to provide secondary teeth 510. Secondary teeth 510 may be provided at the edge of a primary tooth 320.

During use, the cutting head member 260, 800 spins about its longitudinal axis 290. As the cutting head spins, secondary teeth 510 engage with the calcar to remove bone. Bone and/or tissue cut from the calcar is then transported along one or more channels of the form of a spiral, concentric and/or radial recessed region in the cutting surface, to remove the bone and/or tissue from the cutting surface. The cutting surface provides a calcar planer that helps plane a surface of a calcar.

Figure 9:
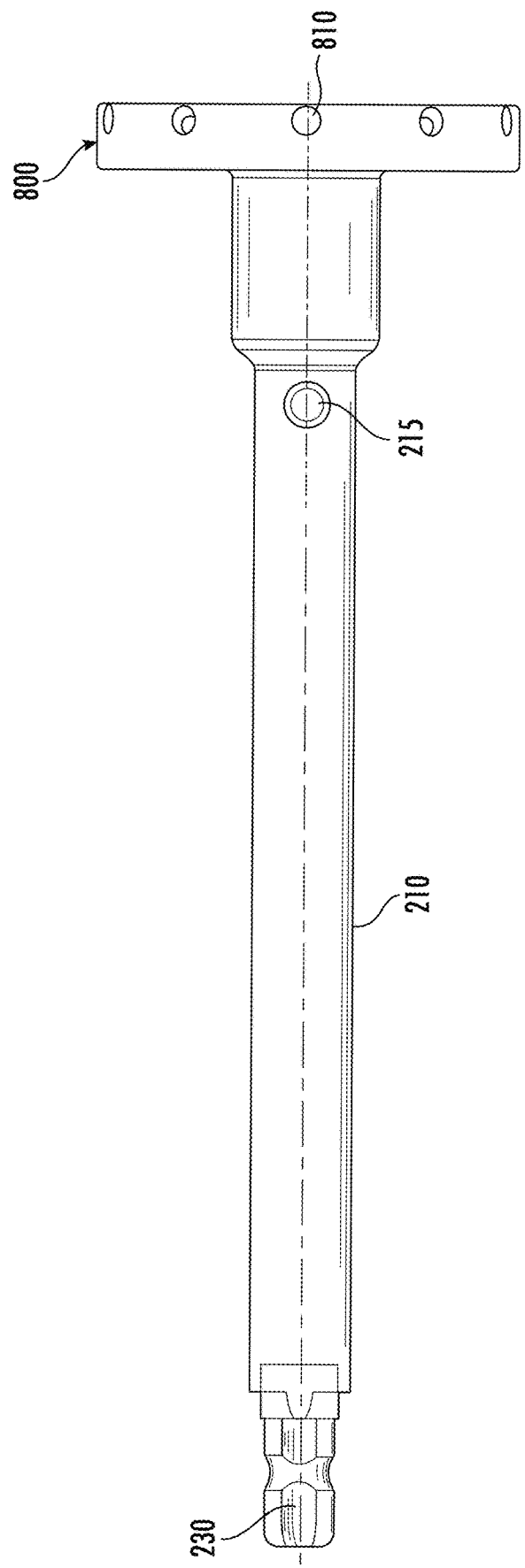
FIG. 9 illustrates a side view of a calcar grinder or planer.
Figure 10:
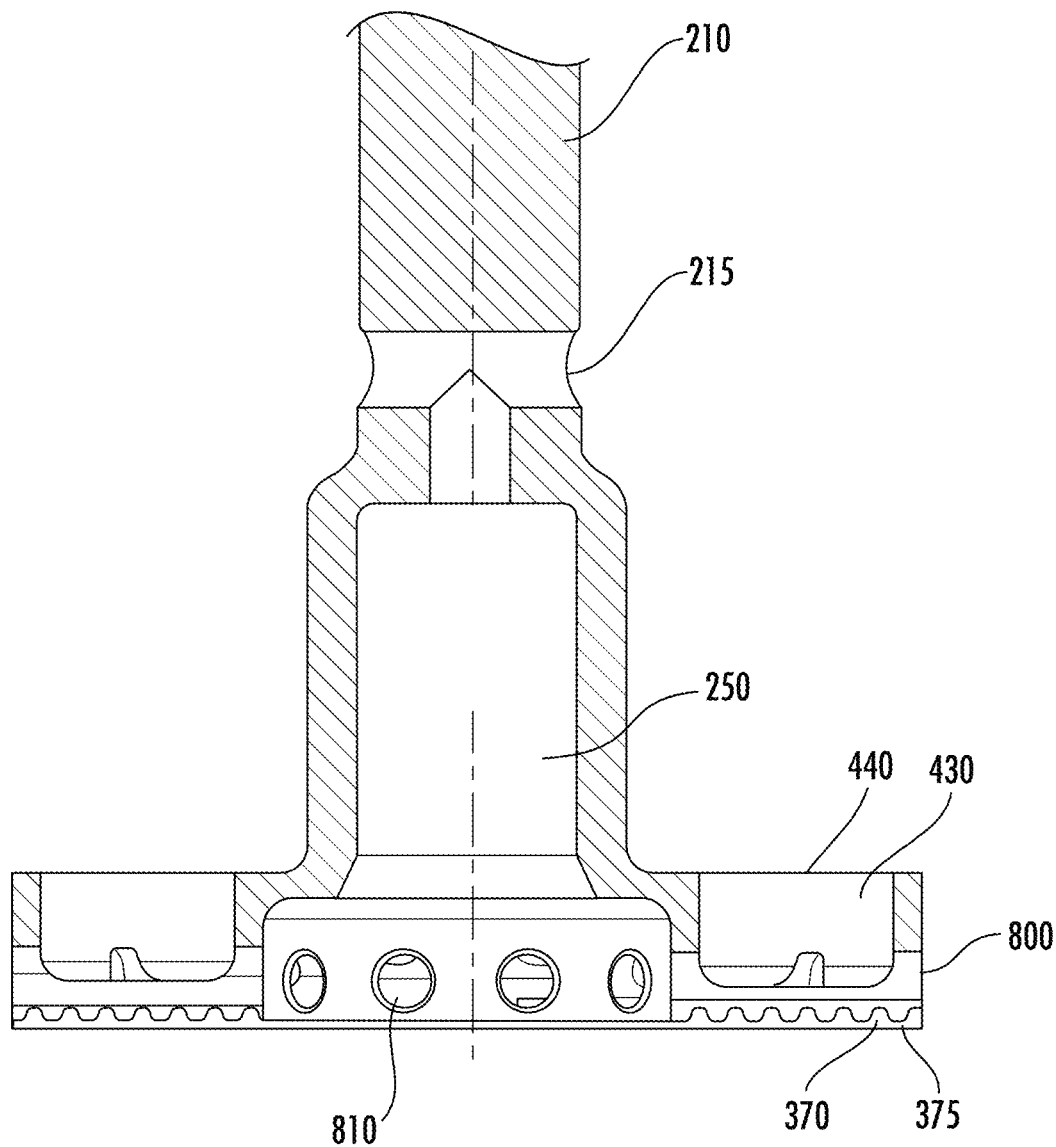
FIG. 10 illustrates a cross-section view of the head end of a calcar grinder.
Figure 11:
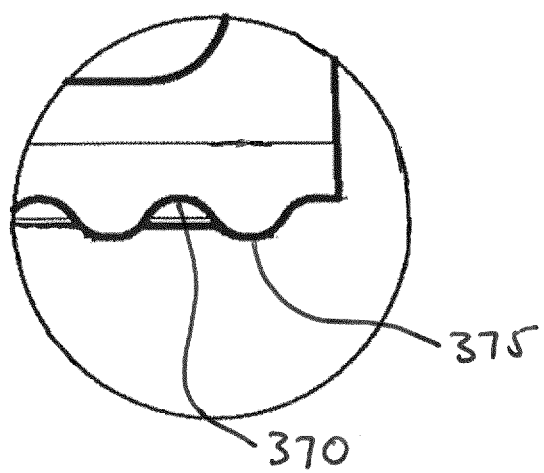
FIG. 11 illustrates a magnified cross-section view of the head end cutting surface of the calcar grinder.

Further views of the alternative cutting head of a calcar grinder shown in FIG. 8 are shown in FIGS. 9 to 11. FIG. 9 shows a calcar grinder viewed side on with a head end 800 illustrating the end of radial recessed regions 810. Aptly, the radial recessed regions 810 have a droplet profile. FIG. 10 shows a cross-section view of the head end of a calcar grinder illustrating a relieving recessed region 430 in a surface 440 of the head end member 800. Ends of radial recessed regions 810 can also be seen in cross-section in FIG. 10. Aptly, the radial recessed regions have a droplet profile. FIG. 11 illustrates a magnified cross-section view of the cutting surface of the cutting head member. Crests 375 and spiral or concentric recessed regions 370 in the cutting surface are shown in cross-section.

It will be appreciated that whilst certain embodiments of the present invention have been described above as having both primary teeth and secondary teeth (and crests and spiral or concentric recessed regions) it will be understood that certain other embodiments of the of the present invention could utilise other combinations of such features.

For example, a cutting head of the present invention may include primary teeth alone, such that each primary tooth of the cutting surface is separated by a radially extending recessed region. Aptly, secondary teeth may also be provided on the cutting surface of the cutting head at a leading edge of each primary tooth.

Alternatively, a cutting head of the present invention may be provided with a spirally extending recessed region in the cutting surface and without primary teeth. Aptly, crests are provided at the cutting surface between portions of the spirally extending recessed region. Aptly, secondary teeth may also be provided on the cutting surface of the cutting head. Aptly, the secondary teeth may be provided as portions of each crest extending out of the plane of the cutting surface.

As a still further alternative, a cutting head of the present invention may include both primary and secondary teeth and spirally extending or concentric recessed regions in the cutting surface. Aptly, crests are provided at the cutting surface between portions of the spiral or concentric recessed regions. Aptly, each primary tooth is separated by a radially extending recessed region. Aptly, secondary teeth may be provided on a leading edge of each primary tooth.

Throughout the description and claims of this specification, the words "comprise" and "contain" and variations of them mean "including but not limited to" and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of the features and/or steps are mutually exclusive. The invention is not restricted to any details of any foregoing embodiments. The invention extends to any novel one, or novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The invention claimed is:

1. An apparatus for removing bone or tissue at a target location, comprising:
   a shaft member having a drive end securable to a rotating drive unit; and
   a cutting head member at a remaining end of the shaft member distal to the drive end;
   wherein:
   the cutting head member includes a cylindrical cutting head body having a cutting surface including a plurality of circumferentially extending radial recessed regions and a plurality of circumferential crests disposed between adjacent revolutions of the plurality of circumferential recessed regions, the cutting head body including a first head member end surface and a second head end surface spaced apart from the first head member end surface via a cylindrical edge region of the cutting head body, the second head end surface including the cutting surface;
   the plurality of circumferential crests include a plurality of teeth thereon;
   each circumferential recessed region is disposed at a distinct distance from a center of the second head member end surface; and
   a central region of the cutting surface is recessed around a position coinciding with a primary longitudinal axis of the shaft member.

2. The apparatus as claimed in claim 1, wherein the plurality of teeth are disposed along a common radius on the cutting surface.

3. The apparatus as claimed in claim 2, wherein the plurality of teeth are disposed at or close to a predetermined radius from a central axis on the cutting surface.

4. The apparatus as claimed in claim 2, wherein the plurality of teeth comprise a plurality of concentric teeth or teeth arranged concentrically.

5. The apparatus as claimed in claim 2, wherein the plurality of teeth are arranged on multiple common concentric circles or on a spiral.

6. The apparatus as claimed in claim 1, wherein the plurality of teeth protrude from a circular cutting surface at a distal end of the shaft member.

7. The apparatus as claimed in claim 1, wherein a central recess is provided in the cutting surface.

8. The apparatus as claimed in claim 1, wherein the plurality of teeth are spaced circumferentially around the cutting surface.

9. The apparatus as claimed in claim 1, further comprising:
   each of the plurality of teeth carries a plurality of secondary teeth.

10. The apparatus as claimed in claim 9, wherein each primary tooth is spaced apart from each adjacent primary tooth via a radially extending channel.

11. The apparatus as claimed in claim 10, wherein each channel comprises a radially extending elongate recess in the cutting surface.

12. The apparatus as claimed in claim 10, wherein each channel meets the cutting surface at an oblique angle.

13. The apparatus as claimed in claim 12, wherein the oblique angle is between 30 to 50 degrees with respect to a longitudinal axis associated with the shaft member.

14. The apparatus as claimed in claim 9, wherein each secondary tooth comprises an upstanding leading edge that extends away from a plane associated with the cutting head member.

15. The apparatus as claimed in claim 9, wherein each secondary tooth further comprises a trailing edge region that lies in a primary plane associated with the cutting surface.

* * * * *